United States Patent
Seto et al.

(10) Patent No.: US 8,337,452 B2
(45) Date of Patent: Dec. 25, 2012

(54) FLUID INJECTION DEVICE

(75) Inventors: Takeshi Seto, Chofu (JP); Kazuo Kawasumi, Chino (JP); Kazuyoshi Takayama, Sendai (JP); Seyed Hamid Reza Hosseini, Seattle, WA (US)

(73) Assignees: Seiko Epson Corporation, Tokyo (JP); Tohoku University, Sendai-Shi (JP)

( * ) Notice: Subject to any disclaimer, the term of this patent is extended or adjusted under 35 U.S.C. 154(b) by 0 days.

(21) Appl. No.: 13/019,575

(22) Filed: Feb. 2, 2011

(65) Prior Publication Data

US 2011/0125086 A1 May 26, 2011

Related U.S. Application Data

(63) Continuation of application No. 11/902,766, filed on Sep. 25, 2007, now Pat. No. 7,901,374.

(30) Foreign Application Priority Data

Sep. 26, 2006 (JP) .................................. 2006-261114

(51) Int. Cl.
*A61M 31/00* (2006.01)

(52) U.S. Cl. ........................................................ 604/48

(58) Field of Classification Search .................... 604/48, 604/131, 891.1; 606/159, 167
See application file for complete search history.

(56) References Cited

U.S. PATENT DOCUMENTS

| | | | |
|---|---|---|---|
| 5,783,072 A | 7/1998 | Kenley et al. | |
| 6,312,409 B1 | 11/2001 | Gross | |
| 6,512,193 B1 | 1/2003 | Moro et al. | |
| 6,604,919 B1 | 8/2003 | Nishio et al. | |
| 6,899,290 B2 | 5/2005 | Varble et al. | |
| 7,094,040 B2 | 8/2006 | Higashino et al. | |
| 7,600,987 B2 | 10/2009 | Seto et al. | |
| 2007/0154336 A1 | 7/2007 | Miyazaki et al. | |

FOREIGN PATENT DOCUMENTS

| | | |
|---|---|---|
| JP | A-63-176679 | 7/1988 |
| JP | A-03-504152 | 9/1991 |
| JP | A-11-107925 | 4/1999 |
| JP | A-2000-145649 | 5/2000 |
| JP | A-2001-153051 | 6/2001 |

(Continued)

OTHER PUBLICATIONS

Sep. 13, 2011 Office Action issued in Japanese Patent Application No. 2009-216719 (with translation).
Oct. 18, 2011 Office Action issued in Japanese Patent Application No. 2006-261114 (with translation).

*Primary Examiner* — Kevin C Sirmons
*Assistant Examiner* — Imani Hayman
(74) *Attorney, Agent, or Firm* — Oliff & Berridge, PLC

(57) ABSTRACT

A fluid injection device includes: a pulse generation section that includes a fluid chamber whose volume is changeable, and an inlet flow passage and an outlet flow passage that are connected to the fluid chamber; a first connection flow passage connected to the outlet flow passage, having an end portion; a second connection flow passage connected to the inlet flow passage; a fluid injection opening formed at the end portion of the first connection flow passage, having a diameter smaller than the diameter of the outlet flow passage; a connection flow passage tube including the first connection flow passage and having rigidity adequate to transmit pulses of fluid flowing from the fluid chamber to the fluid injection opening; and a pressure generation section that supplies fluid to the inlet flow passage.

7 Claims, 6 Drawing Sheets

FOREIGN PATENT DOCUMENTS

| | | |
|---|---|---|
| JP | A-2002-130135 | 5/2002 |
| JP | A-2003-239866 | 8/2003 |
| JP | A-2004-116327 | 4/2004 |
| JP | A-2004-162547 | 6/2004 |
| JP | A-2004-180841 | 7/2004 |
| JP | A-2005-152127 * | 6/2005 |
| JP | A-2005-282498 | 10/2005 |
| JP | A-2005-307743 | 11/2005 |
| WO | WO 90/07648 A1 | 7/1990 |
| WO | WO 99/61191 A1 | 12/1999 |

* cited by examiner

ND DEVICE

CROSS-REFERENCE TO RELATED APPLICATION

This is a Continuation of application Ser. No. 11/902,766 filed Sep. 25, 2007. The disclosure of the prior application is hereby incorporated by reference herein in its entirety.

This application claims priority from Japanese Patent Application No. 2006-261114, filed on Sep. 26, 2006, the contents of which are incorporated herein by reference.

BACKGROUND

1. Technical Field

The present invention relates to a fluid injection device. More specifically, the present invention relates to a fluid injection device of simple construction that injects stable and strong pulses of fluid.

2. Related Art

Conventional fluid injection device as disclosed in the Japanese Unexamined Patent Application, First Publication No. 2005-152127, for example, is well known as a fluid injection device for dissecting or cutting out biopsy tissues.

This fluid injection device includes a micro-pump, a connection flow passage, and a connection tube.

The micro-pump changes the volume of the pump chamber and discharges the fluid.

The outlet flow passage of the micro-pump is connected to one end of the connection flow passage, and an opening (nozzle) made smaller than the diameter of the outlet flow passage is formed at another end of the connection flow passage.

The connection tube has a rigidity that is adequate to transmit the pulses of the fluid flowing from the micro-pump in which the connection flow passage to the opening is formed.

The fluid flows in this fluid injection device by repetitive pulse wave trains and pauses, and is injected at high speed from the opening.

In the Japanese Unexamined Patent Application, First Publication No. 2005-307743, the art of providing a piston pump and a pump priming device on the side of the outlet flow passage of the micro-pump configured as mentioned above, is disclosed.

According to this art, the priming operation is performed at start when fluid has not entered the micro-pump, and the air in the pump chamber is compressed and removed after the start of operation.

According to Japanese Unexamined Patent Application, First Publication No. 2005-152127, pulsating fluid can be injected at high speed and can be easily controlled.

While the ability to dissect tissues during surgery, for example, is high, the quantity of injection of pulsating fluid was low, and fluid rarely accumulated in the surgical field.

Consequently, visibility was enhanced and the scattering of tissues was effectively prevented.

This micro-pump required priming operation and elimination of air bubbles in the pump chamber at the start of operation based on the operating characteristics, and a construction with installation of the pump priming device as disclosed in the Japanese Unexamined Patent Application, First Publication No. 2005-307743, was proposed.

However, even if a pump priming device is installed, the priming device is disconnected and removed after start, and when air bubbles are generated in the pump chamber, the drive operation may become unstable.

Also, in the micro-pump according to the Japanese Unexamined Patent Applications, First Publication No. 2005-152127 and First Publication No. 2005-307743, the inertance on the outlet flow passage side is set greater than the inertance on the inlet flow passage side; thus, a check valve was installed on the inlet flow passage side to prevent back flow of the fluid.

This check valve is extremely small, and its washability is poor. Also, the check valve may not be able to maintain adequate performance for long period use or repetitive use.

SUMMARY

An advantage of an aspect of the invention is to provide a fluid injection device in which it is possible to realize a simple construction having high reliability, to eliminate degradation in performance due to accumulation of air bubbles during operation, and it is not necessary a priming device.

An aspect of the invention provides a fluid injection device of the invention including: a pulse generation section that includes a fluid chamber whose volume is changeable, and an inlet flow passage and an outlet flow passage that are connected to the fluid chamber; a first connection flow passage connected to the outlet flow passage, having an end portion; a second connection flow passage connected to the inlet flow passage; a fluid injection opening formed at the end portion of the first connection flow passage, having a diameter smaller than the diameter of the outlet flow passage; a connection flow passage tube including the first connection flow passage and having rigidity adequate to transmit pulses of fluid flowing from the fluid chamber to the fluid injection opening; and a pressure generation section that supplies fluid to the inlet flow passage.

As the pressure generation section, a pump discharging fluid at constant pressure may be used, for example.

According to this invention, the fluid is supplied to the inlet flow passage at a constant pressure from the pressure generation section. Even if the drive of the pulse generation section is in the stop condition, fluid is supplied to the inlet flow passage and the fluid chamber. Therefore, priming operation is not required, and the initial operation can be started.

Moreover, the fluid can be injected at high speed because fluid is injected from a fluid injection opening which has been made smaller than the diameter of the outlet flow passage.

Furthermore, since the connection flow passage tube has adequate rigidity to transmit the pulses of the fluid flowing from the fluid chamber to the opening, the propagation of fluid pressure from the pulse generation section is not obstructed, and the desired pulse flow can be injected.

It is preferable that, in the fluid injection device of the aspect of the invention, the inertance of the inlet flow passage be set greater than the inertance of the outlet flow passage.

In this structure, by driving the pulse generation section, the pulse flow with inflow rate of fluid greater than that of the pulse flow from the inlet flow passage to the fluid chamber is generated in the outlet flow passage. The fluid in the pulsed state can be discharged into the connection flow passage tube.

Consequently, there is no need to install a check valve on the inlet flow passage side, as in the Japanese Unexamined Patent Application, First Publication No. 2005-152127, the construction of the pulse generation section becomes simpler, internal parts can be easily cleaned, and the concern about durability because of using a check valve can also be eliminated.

If the inertance of both the inlet flow passage and the outlet flow passage is set adequately great, and if the volume of the fluid chamber is abruptly reduced, then the pressure in the fluid chamber steeply increases.

Thus, a pulse flow which is greater than that of the outlet flow passage can be generated.

It is preferable that, in the fluid injection device of the aspect of the invention, the pulse generation section include a volume varying section for varying the volume of the fluid chamber, and the volume varying section include a piezoelectric element that expands or compresses the fluid chamber, and a diaphragm.

If a piezoelectric element is used as the volume varying section, the structure can be simplified, and as a result the pulse generation section can be made smaller.

The maximum frequency of change in volume of the fluid chamber can be set at greater than or equal to 1 kHz, which is ideal for injection of pulsed flow at high speed and at short repetitive periods.

It is preferable that the fluid injection device of the aspect of the invention further include: a swirl flow generation section generating swirl flow of fluid around an axis of the fluid chamber. In this structure, the fluid chamber has a substantial rotating body shape, and includes an inner peripheral wall having a first end and a second end, a sealing surface sealing the first end of the inner peripheral wall, and a diaphragm sealing the second end of the inner peripheral wall. Also, in this structure, the outlet flow passage is formed at a portion which is closer to the axis of the substantial rotating body shape.

The rotating body shape may be selected from cylindrical shape, conical shape, hemispherical shape, or the like.

By generating a swirl flow in the fluid in the fluid chamber using the swirl flow generation section, the fluid is pushed toward the fluid chamber in the circumferential direction by centrifugal force. The air bubbles included in the fluid near the axis of the substantial rotating body shape accumulate at the center of the swirl flow. These air bubbles can be removed from the outlet flow passage formed at a portion which is closer to the axis of the substantial rotating body shape.

As a result, the reduction in pressure amplitude due to the existence of air bubbles in the fluid chamber can be prevented. Also, the pulse generation section can be driven stably and continuously.

It is preferable that, in the fluid injection device of the aspect of the invention, the swirl flow generation section be formed by the inlet flow passage that connects the inner peripheral wall of the fluid chamber in a substantially tangential direction.

In this structure, since the swirl flow generation section is formed by the inlet flow passage, swirl flow can be generated and there is no need to use a special swirl flow generation section.

The inner peripheral wall of the fluid chamber is equivalent to the outer surface of the substantial rotating body shape.

It is preferable that, in the fluid injection device of the aspect of the invention, the inlet flow passage be formed on the peripheral edge of the fluid chamber.

To form an inlet flow passage in this structure, a groove may be formed on the peripheral edge of the fluid chamber, for example, as the inlet flow passage.

Consequently, inlet flow passage may be formed as the swirl flow generation section without increasing the number of parts.

It is preferable that, in the fluid injection device of the aspect of the invention, the swirl flow generation section be formed by a swirl flow generation plate that includes the inlet flow passage and the inner peripheral wall of the fluid chamber.

By forming the swirl flow generation section by a swirl flow generation plate in this structure, the inlet flow passage and the inner peripheral wall may be easily formed by the pressing process, etching process, or the like.

Moreover, if various types of swirl flow generation plate having different cross-sectional areas and lengths of the inlet flow passage are kept ready, then the desired inertance can be selectively set on the inlet flow passage side.

It is preferable that, in the fluid injection device of the aspect of the invention, the swirl flow generation plate and the diaphragm be stacked and attached in intimate contact as an integral body.

The swirl flow generation plate is made of thin plate. An opening having the inner peripheral wall of the fluid chamber and the inlet flow passage is formed on the swirl flow generation plate.

The structural strength to resist high pressure addition within the fluid chamber is likely to be inadequate. In this structure, by making the plate integral with the diaphragm, adequate structural strength can be obtained.

Another advantage is that handling is easy during assembly.

It is preferable that the fluid injection device of the aspect of the invention further include: a reinforcing plate that has an opening whose diameter is substantially equal to the diameter of the fluid chamber, and that is formed between the sealing surface on which the inlet flow passage is formed or the swirl flow generation plate, and the diaphragm.

The inlet flow passage and an opening that forms inner peripheral wall of fluid chamber are formed in the swirl flow generation plate.

In this case, the opening and inlet flow passage merge into a merged portion, which is in the shape of a notch.

Since the diaphragm takes the periphery of the opening as the drive support point, stress concentration occurs in the merged portion.

However, by providing the reinforcing plate, the diaphragm takes the periphery of the opening of the reinforcing plate as the support point. Thus, stress concentration does not occur easily, and the durability of the diaphragm can be enhanced.

It is preferable that, in the fluid injection device of the aspect of the invention, the swirl flow generation plate and the reinforcing plate be stacked and attached in intimate contact with each other as an integral body.

In this structure, the swirl flow generation plate can be reinforced, and handling during assembly becomes easy.

It is preferable that, in the fluid injection device of the aspect of the invention, the diaphragm and the reinforcing plate be stacked and attached in intimate contact with each other as an integral body.

In this structure, the swirl flow generation plate can be indirectly reinforced, and handling during assembly becomes easy.

It is preferable that the fluid injection device of the aspect of the invention further include: a fluid basin that be formed at the connection between the second connection flow passage on the inlet side supplying fluid to the inlet flow passage from the pressure generation section and the inlet flow passage, that collects fluid.

The direction of flow of fluid and the cross-sectional area of the flow passage change at the connection of the second connection flow passage on the inlet side and the inlet flow passage. The characteristics of the second connection flow passage on the inlet side are considered to affect the characteristics of the inlet flow passage.

By installing a fluid basin at the connection, the velocity head in the second connection flow passage on the inlet side becomes extremely small; thus the influence on the inlet flow passage due to the second connection flow passage on the inlet side can be inhibited.

It is preferable that, in the fluid injection device of the aspect of the invention, the inlet flow passage be formed by a tubular member that passes through the fluid chamber and an exterior of the pulse generation section.

If the inlet flow passage is formed by a tubular member, the cross-sectional shape of the flow passage can be made circular, and the resistance elements in the flow passage can be reduced.

The inside diameter and length of the tubular member can be easily set. Moreover, the cross-sectional area of the inlet flow passage and the length of the flow passage can be easily set to match the inertance setting on the inlet flow passage side.

It is preferable that the fluid injection device of the aspect of the invention further include: a ring-shaped packing separately disposed at a position in the circumferential direction of the diaphragm.

The diaphragm is a member that seals a part of the fluid chamber.

As mentioned above, since the internal parts of the fluid chamber is at high pressure, fluid may leak at the connection of the diaphragm.

If fluid leaks from the fluid chamber, the pressure does not rise to the desired level.

By providing a packing, the fluid leakage can be prevented, and the rise of pressure in the fluid chamber is not hindered.

DESCRIPTION OF EXEMPLARY EMBODIMENTS

Figure 1:
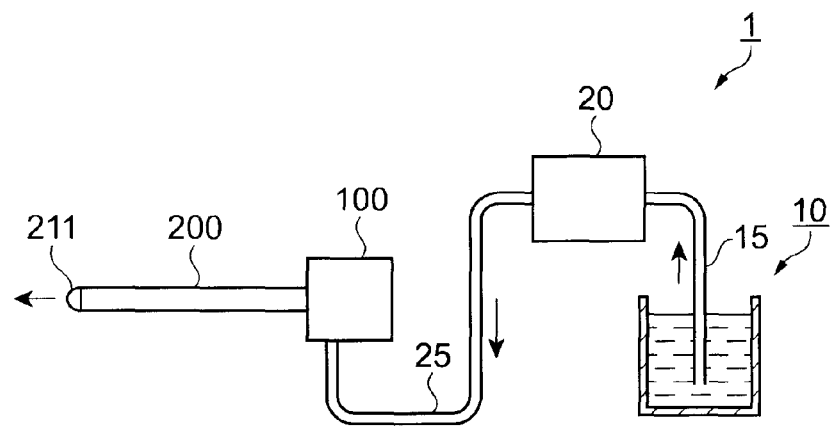
FIG. 1 is an explanatory schematic diagram of a configuration of a fluid injection device of a first embodiment of the invention.

The embodiments of the invention are described hereafter referring to the drawings.

Figure 2:
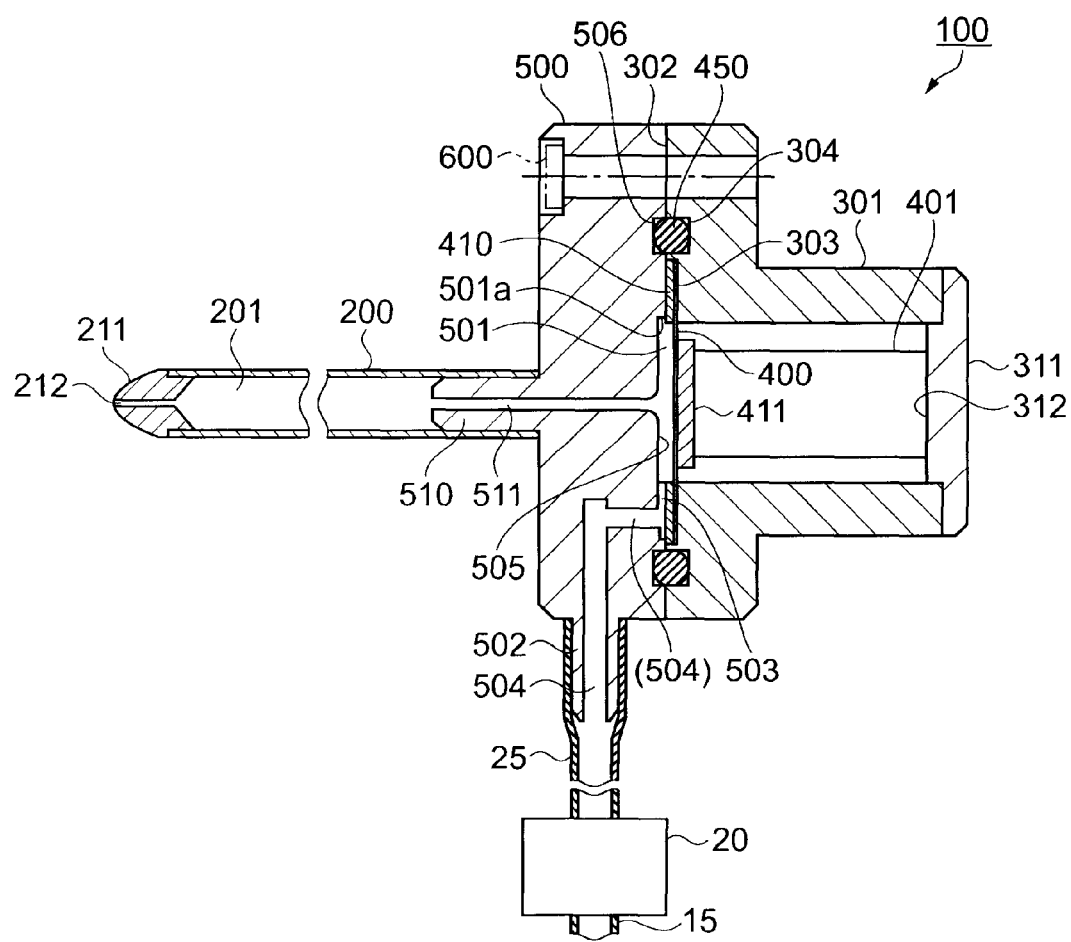
FIG. 2 is a cross-sectional view of a configuration of a pulse generation section of the first embodiment of the invention.
Figure 3:
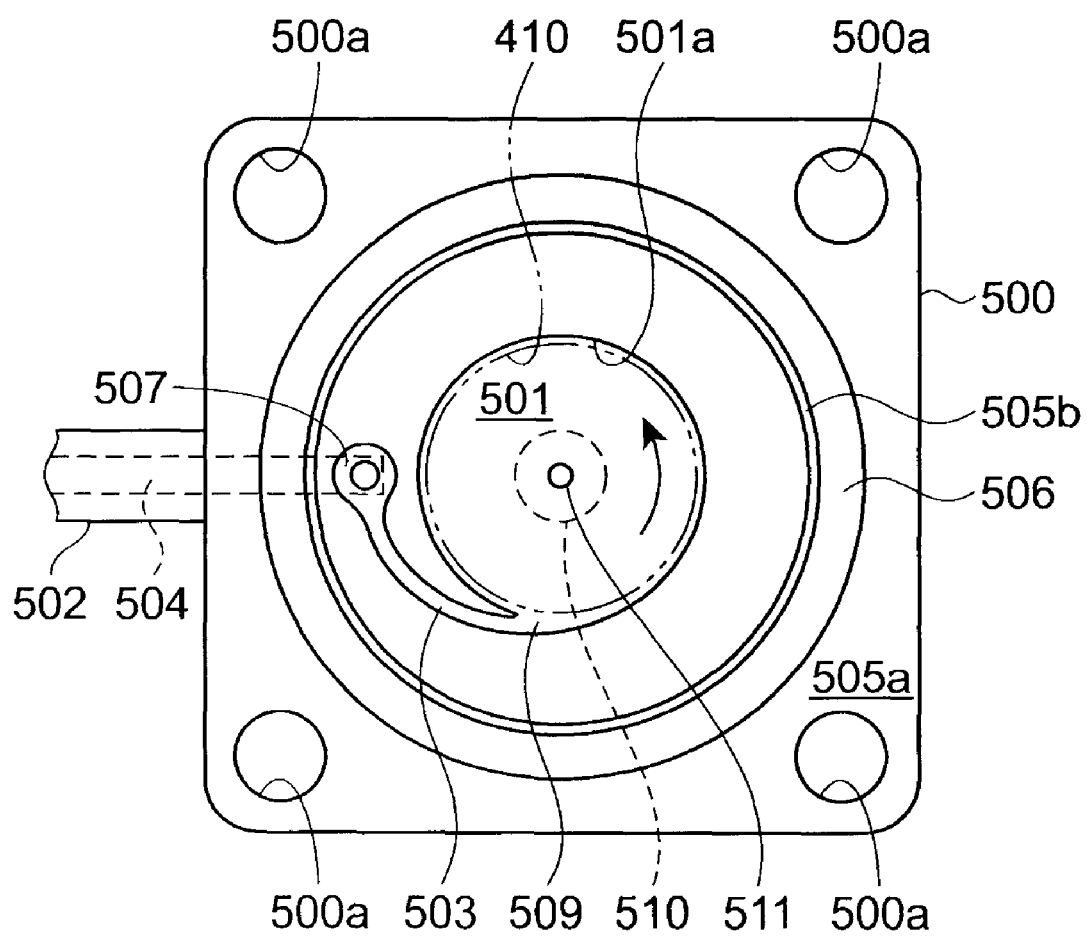
FIG. 3 is a plan view of an inlet flow passage of the first embodiment of the invention.

FIGS. 1 to 3 show the fluid injection device and the pulse generating section related to the first embodiment.

Figure 4:
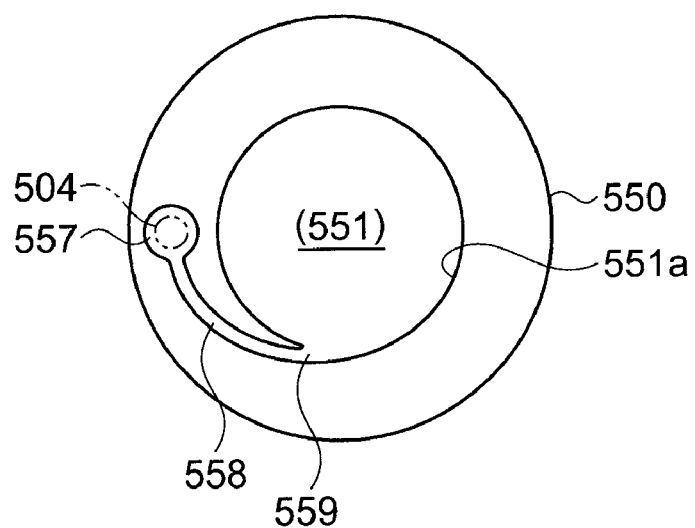
FIG. 4 is a plan view of a swirl flow generation plate of a second embodiment of the invention.
Figure 5:
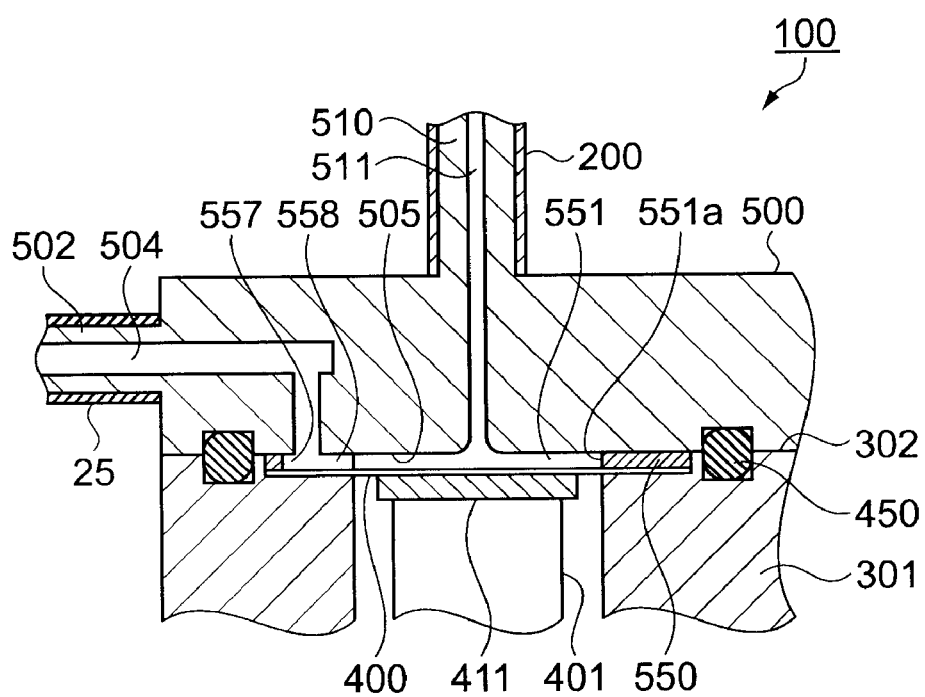
FIG. 5 is a cross-sectional view of the pulse generation section in which the swirl flow generation plate is assembled of the second embodiment of the invention.

FIGS. 4 and 5 show the pulse generating section related to the second embodiment.

Figure 6:
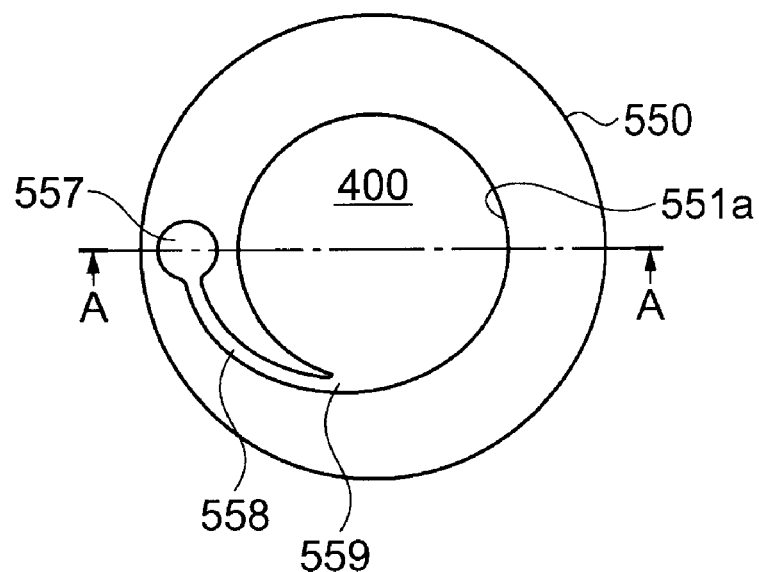
FIG. 6 is a plan view of a diaphragm connected to the swirl flow generation plate of a third embodiment of the invention.
Figure 7:
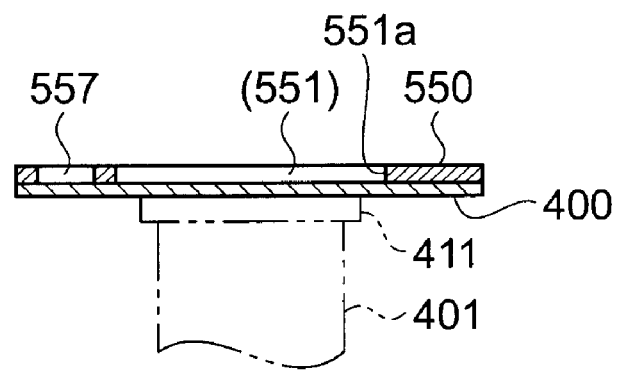
FIG. 7 is a cross-section view taken along the line A-A shown in FIG. 6.

FIGS. 6 and 7 show the pulse generating section related to the third embodiment.

Figure 8A:
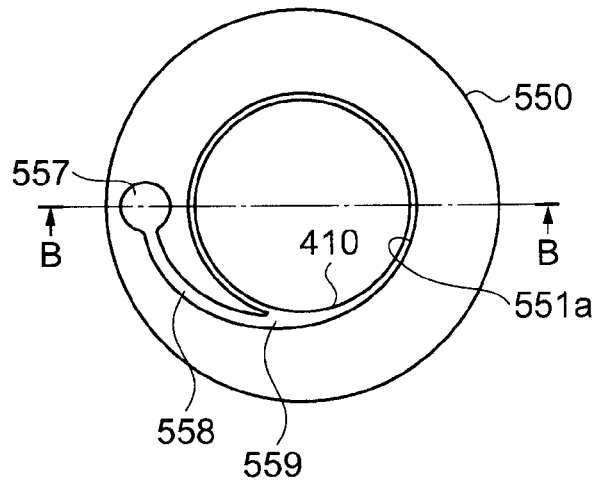
FIG. 8A is a plan view showing the connected state of the reinforcing plate and the swirl flow generation plate of a fourth embodiment of the invention.
Figure 8B:
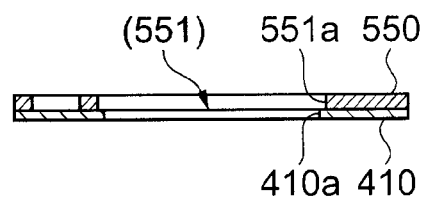
FIG. 8B is a cross-sectional view taken along the line B-B shown in FIG. 8A.
Figure 9:
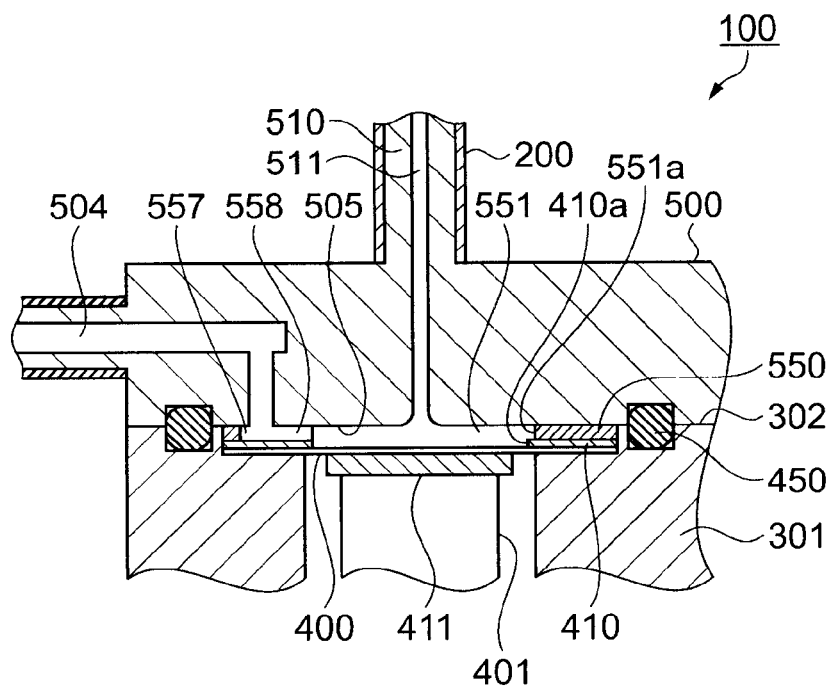
FIG. 9 is a cross-sectional view of the pulse generation section of the fourth embodiment of the invention.

FIGS. 8A, 8B, and 9 show the pulse generating section related to the fourth embodiment.

Figure 10:
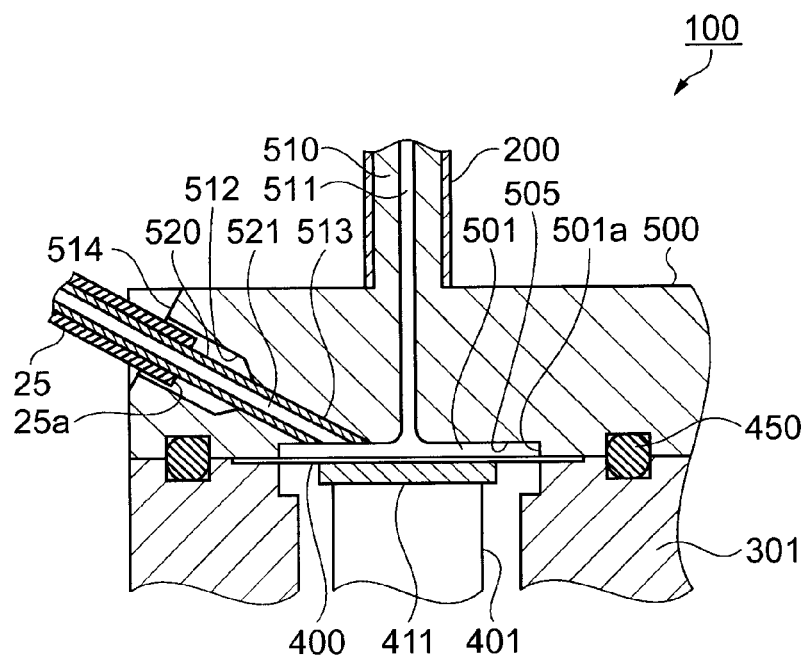
FIG. 10 is a cross-sectional view of the pulse generation section of a fifth embodiment of the invention taken along the line C-C shown in FIG. 11.
Figure 11:
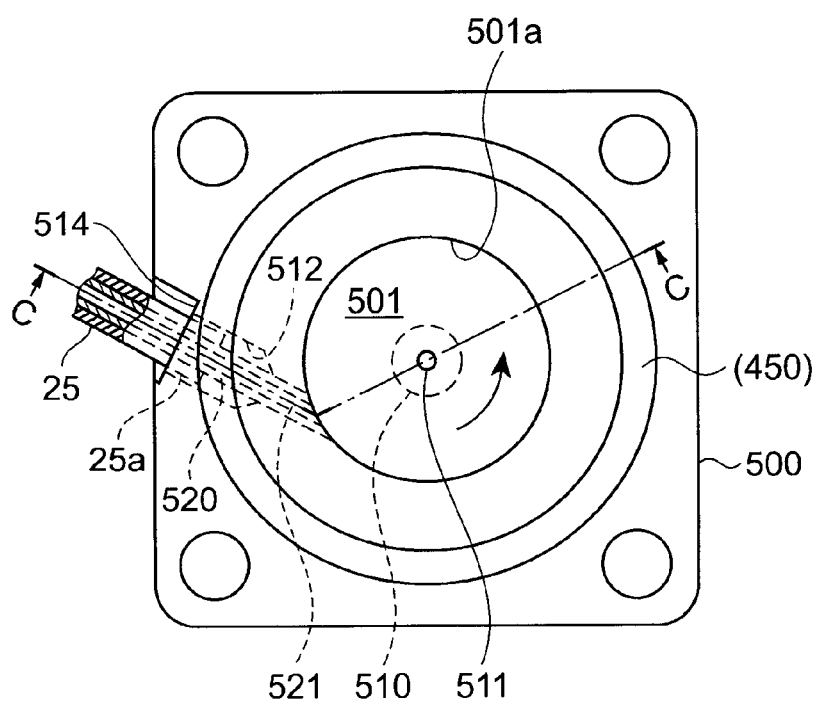
FIG. 11 is a plan view showing the condition of the upper case related to the fifth embodiment of the invention observed from the lower case side.

FIGS. 10 and 11 show the pulse generating section related to the fifth embodiment.

The embodiments described hereafter are detailed examples preferred for the invention and are subjected to various technically preferred limitations. The scope of the invention is not limited to these embodiments unless the limitation on the invention is expressly stated in the description below.

The figures referred to in the description below, are schematic drawings, and the scale on the vertical axis of members and/or parts may differ from the actual scale.

The fluid injection device according to the invention may be used in various applications such as in drawing using ink and so on, in cleaning dense substances and structural items, and for surgical blades. In the embodiments described below, a fluid injection device that is ideal for dissecting or cutting out biopsy tissue is used as an example in the description.

Consequently, the fluid used in the embodiment is water or saline solution.

First Embodiment

FIG. 1 is an explanatory schematic diagram of the configuration of the fluid injection device related to the first embodiment of the invention.

In FIG. 1, the fluid injection device 1 includes a fluid container 10 containing the fluid as the basic configuration, a pump 20 as the pressure generation section, and a pulse generation section 100 generating a pulse flow of the fluid supplied from the pump 20.

A slender tubular shaped connection flow passage tube 200 is connected to the pulse generation section 100.

A nozzle 211 with its flow passage compressed is inserted in the front end of the connection flow passage tube 200.

The flow of the fluid in the fluid injection device 1 is described below in a simple manner.

The fluid contained in the fluid container 10 is drawn in by the pump 20 through a connection tube 15, and is supplied to the pulse generation section 100 at constant pressure through a connection tube 25.

As shown in FIG. 2, the pulse generation section 100 includes a fluid chamber 501, and a volume varying section of this fluid chamber 501. The pulse generation section 100 drives the volume varying section and generates pulses, and injects the fluid at high speed through the connection flow passage tube 200 and the nozzle 211.

Detailed explanations on the pulse generation section 100 are given later referring to FIGS. 2 and 3.

The pressure generation section is not limited to pump 20; a liquid transport bag maintained at a position higher than the pulse generation section 100 by a stand or the like may be used.

Accordingly, the advantages are: the pump 20 is not necessary, the configuration becomes simpler, and disinfection is easy.

The discharge pressure of the pump 20 is set at lower than or equal to 0.3 atmosphere (0.03 MPa).

If the liquid transport bag is used, the difference in height of the liquid upper surface of the pulse generation section 100 and the liquid transport bag becomes the pressure.

If the liquid transport bag is used, it is preferable that the difference in height be set such that the pressure is in the range of 0.1 to 0.15 atmosphere (0.01 to 0.15 MPa).

When performing surgery using the fluid injection device 1, the surgeon grasps the pulse generation section 100.

Consequently, it is preferable that the connection tube 25 from the pump 20 to the pulse generation section 100 be as flexible as possible.

For this reason, it is preferable that the tube be flexible and thin, and the fluid in the pulse generation section 100 be at low pressure within the pumpable range.

Also, when a fault in the equipment may lead to a major accident, as in brain surgery, the discharge of fluid at high pressure due to a cut in the connection tube 25 must be avoided; for this reason also, the fluid must be at low pressure.

Next, the construction of the pulse generation section 100 according to the first embodiment is described here.

FIG. 2 is a cross-sectional view of the configuration of the pulse generation section 100 of the first embodiment.

As shown FIG. 2, the pulse generation section 100 includes a pulse generating device for generating pulse in the fluid. The connection flow passage tube 200 having a connection flow passage (first connection flow passage) 201 for discharging fluid is connected to the pulse generation section 100.

The pulse generation section 100 is joined at the surfaces opposite to an upper case 500 and a lower case 301 respectively. The upper case 500 and the lower case 301 are screwed in with four securing screws 600 (not shown in the drawings).

The lower case 301 is a cylindrical member having a collar. A portion of the lower case 301 opposite to the upper case 500 is sealed by the base plate 311.

A piezoelectric element 401 is disposed in the space within the lower case 301.

The piezoelectric element 401 is a stacked-type piezoelectric element and constitutes an actuator.

The first end of the piezoelectric element 401 is fixed to diaphragm 400 through upper plate 411, and the second end of the piezoelectric element 401 is fixed to the upper surface 312 of the base plate 311.

Also, the diaphragm 400 is made of a disc-shaped thin metallic plate. The peripheral edge in the groove 303 of the lower case 301 is fixed in intimate contact with the bottom surface of the groove 303.

When a drive signal is input to the piezoelectric element 401 used as the volume varying section, the volume of the fluid chamber 501 changes through the diaphragm 400 with the extension and shrinkage of the piezoelectric element 401.

A reinforcing plate 410 made of disc-shaped thin metallic plate having an opening at the center is stacked and disposed on the upper surface of the diaphragm 400.

A groove is formed at the central part of the surface of the upper case 500 opposite to the lower case 301. A fluid chamber 501 in the shape of a rotating body and filled with fluid is made of this groove and the diaphragm 400.

That is, the fluid chamber 501 includes a space enclosed by the sealing surface 505 of the groove of the upper case 500, the inner peripheral wall 501a, and the diaphragm 400.

An outlet flow passage tube 510 is formed to protrude from the end face of the upper case 500 opposite to the lower case 301.

An outlet flow passage 511 is formed at substantially the center of the fluid chamber 501.

The outlet flow passage 511 is a through passage from the fluid chamber 501 to the end of the outlet flow passage tube 510.

The connection between the sealing surface 505 and the outlet flow passage 511 is smoothly rounded to reduce the fluid resistance.

As shown FIG. 2, the fluid chamber 501 described above in the first embodiment has a substantially cylindrical and sealed shape at the two ends, but when viewed from the side, the surface has no limitation. As the shape, conical, trapezoidal or hemispherical may be adopted.

For example, if the connection between the outlet flow passage 511 and the sealing surface 505 is made in the shape of a funnel, air bubbles in the fluid chamber 501 mentioned later, can be easily removed.

A connection flow passage tube 200 is connected to the outlet flow passage 510.

A connection flow passage 201 is formed in the connection flow passage tube 200. The diameter of the connection flow passage 201 is grater than the diameter of the outlet flow passage 511.

The thickness of the tubing portion of the connection flow passage tube 200 is kept within a range such that the connection flow passage tube 200 has adequate rigidity yet does not absorb the pressure pulses of the fluid.

A nozzle 211 attached by insertion to the front end of the connection flow passage tube 200.

A fluid injection opening 212 is formed in this nozzle 211. Thus, the fluid injection opening 212 is formed at the end portion of the connection flow passage 201.

The diameter of the fluid injection opening 212 is smaller than the diameter of the connection flow passage 201.

An inlet flow passage tube 502 is formed to protrude from the side face of the upper case 500. The inlet flow passage tube 502 is inserted into the connection tube 25. The inlet flow passage tube 502 supplies fluid from the pump 20.

A connection flow passage (second connection flow passage) 504 is formed on the side of the inlet flow passage in the inlet flow passage tube 502.

An inlet flow passage 503 is connected with the connection flow passage 504.

The inlet flow passage 503 is formed in a groove shape in the peripheral edge of the sealing surface 505 of the fluid chamber 501, and is connected with the fluid chamber 501.

At a position which is separated from the diaphragm 400 in the circumferential direction, and on the connection surface between the upper case 500 and the lower case 301, a packing box 304 is formed on the side of the lower case 301 and a packing box 506 is formed on the side of the upper case 500, and a ring-shaped packing 450 is attached in the space formed by the packing boxes 304 and 506.

When assembling the upper case 500 and the lower case 301, the peripheral edge of the diaphragm 400 and the peripheral edge of the reinforcing plate 410 are brought into close contact by the bottom surface of the groove 303 of the lower case 301 and the peripheral edge of the sealing surface 505 of the upper case 500.

In this case, the packing 450 is pressed by the upper case 500 and the lower case 301, and fluid leakage from the fluid chamber 501 is prevented.

When the pressure inside the fluid chamber 501 increases to a high pressure above 30 atmospheres (3 MPa) when fluid is discharged, a small amount of fluid could leak in the connections of the diaphragm 400, reinforcing plate 410, upper case 500, lower case 301, respectively, but this leak is prevented by the packing 450.

When packing 450 is disposed as shown in FIG. 2, the pressure of fluid that leaks at high pressure from the fluid chamber 501 compresses the packing 450, and the walls in the packing box 304 and 506 are pressed with a strong force; thus, the leakage of fluid can be more firmly prevented.

As a result, the rise in high pressure in the fluid chamber 501 can be maintained during the operation.

Next, the inlet flow passage 503 formed in the upper case 500 is described in further detail referring to the drawings.

FIG. 3 is a plan view of the inlet flow passage 503, and indicates the state when the upper case 500 is viewed from the side of the connecting face with the lower case 301.

The inlet flow passage 503 in FIG. 3 is formed in the shape of a peripheral edge groove of the sealing surface 505 of the upper case 500.

The inlet flow passage 503 connects with the fluid chamber 501 at the first end of the inlet flow passage 503. The inlet flow passage 503 connects with the connection flow passage 504 at the second end of the inlet flow passage 503.

A fluid basin 507 is formed at the connection between the inlet flow passage 503 and the connection flow passage 504.

The fluid resistance is reduced by smoothly rounding the connection between the fluid basin 507 and the inlet flow passage 503.

The inlet flow passage 503 is connected with the fluid chamber 501 in the substantially tangential direction to the inner peripheral wall 501a of the fluid chamber 501.

As shown in FIG. 1, the fluid supplied at constant pressure from the pump 20 flows along the inner peripheral wall 501a (direction shown by arrow in FIG. 3), and generates a swirl flow in the fluid chamber 501.

The swirl flow presses against the side of the inner peripheral wall 501a due to centrifugal force because of the swirling motion, and the air bubbles included in the fluid chamber 501 concentrate at the center of the swirl flow.

The air bubbles that have collected at the center are removed from the outlet flow passage 511.

Thus, it is preferable that the outlet flow passage 511 be installed near the center of the swirl flow. It is preferable that the outlet flow passage 511 be installed at the center of the axis of the rotating shape body.

Consequently, the inlet flow passage 503 is a swirl flow generation section in the first embodiment.

In FIG. 3, the inlet flow passage 503 is curved in a plane form.

The inlet flow passage 503 may be connected the fluid chamber 501 in a straight line. In order to obtain the desired inertance in a narrow space, the inlet flow passage 503 is curved. Because it is necessary to make the flow passage length of the inlet flow passage 503 long.

As shown in FIG. 2, a reinforcing plate 410 is disposed between the diaphragm 400 and the peripheral edge of the sealing surface 505 in which the inlet flow passage 503 is formed.

The reinforcing plate 410 is installed to enhance the durability of the diaphragm 400.

Since a connection opening 509 is formed in notch shape in the connection between the inlet flow passage 503 and the fluid chamber 501, stress concentration occurs near the connection opening 509 and fatigue failure may occur, when the diaphragm 400 is driven at a high frequency.

Therefore, a reinforcing plate 410 with a continuous opening and no notch is disposed so that stress concentration does not occur in the diaphragm 400.

Screw holes 500a are formed at four locations at the corners of the outer periphery of the upper case 500. The upper case 500 and the lower case 301 are screwed together and connected at these screw hole positions.

The reinforcing plate 410 and the diaphragm 400 may be connected and may be stacked fixed together to form an integral body, although this arrangement is not shown in the drawings.

As fixing structure, adhesive may be used to attach the items, or solid state diffusion bonding, welding or the like may be used. It is preferable that the reinforcing plate 410 and the diaphragm 400 be in close contact at the connecting face.

Next, the operation of the first embodiment is described here referring to FIGS. 1 to 3.

The fluid discharge of the pulse generation section 100 of the first embodiment is performed according to the difference between the inertance L1 (synthesized inertance L1 may sometimes be called) on the inlet flow passage side and the inertance L2 on the outlet flow passage side (synthesized inertance L2 may sometimes be called).

Inertance is first described below.

The inertance L may be expressed by $L=\rho \times h/S$, where density of fluid is $\rho$, cross-sectional area of flow passage is S, and the length of the flow passage is h.

If the differential pressure in the flow passage is taken as $\Delta P$, and the flow rate of fluid flowing in the flow passage as Q, then the equation of motion in the flow passage using inertance L may be modified to obtain the relationship $\Delta P = L \times dQ/dt$.

That is, the inertance L indicates the influence level on the change with time of flow rate. The greater the inertance L, the smaller is the change with time of the flow rate; the smaller the inertance L, the greater is the change with time of the flow rate.

The synthesized inertance related to parallel connections of a plurality of flow passages or direct connections of a plurality of flow passages with varying shapes can be calculated by combining the inertance of individual flow passages, similar to parallel connections or direct connections of inductance in an electric circuit.

For the inertance L1 on the inlet flow passage side, since the diameter of the connection flow passage 504 is set adequately greater than that of the inlet flow passage 503, the inertance L1 can be calculated in the range of the inlet flow passage 503.

In this case, since the connection tube connecting the pump 20 and the inlet flow passage has flexibility, the connection tube may not be considered in the calculation of inertance L1.

In case of the inertance L2 on the outlet flow passage side, the diameter of the connection flow passage 201 is much greater than the outlet flow passage, and the thickness of the tube portion (tube wall) of the connection flow passage tube 200 is small, therefore the influence on the inertance L2 is negligible.

Consequently, the inertance L2 on the outlet flow passage side may be replaced with the inertance of the outlet flow passage 511.

The thickness of the tube wall of the connection flow passage tube 200 is such that it has adequate rigidity to transmit the fluid pressure.

In the first embodiment, the length and cross-sectional area of the flow passage of the inlet flow passage 503, and the length and cross-sectional area of the flow passage of the outlet flow passage 511 are set such that the inertance L1 on the side of the inlet flow passage becomes greater than the inertance L2 on the side of the outlet flow passage.

Next, the operation of the pulse generation section 100 is described here.

Fluid is supplied at constant pressure at all times in the inlet flow passage 503 by the pump 20.

As the result, when the piezoelectric element 401 does not operate, the fluid flows into the fluid chamber 501 because of the difference in the value of the fluid resistance of the entire inlet flow passage and the discharge pressure of the pump 20.

Here, if the drive signal is input to the piezoelectric element 401, and if the piezoelectric element 401 extends rapidly, the pressure in the fluid chamber 501 rises sharply and reaches several tens of atmospheres if the inertance L1 and L2 on the side of the inlet flow passage and outlet flow passage are adequately high.

This pressure is much higher than the pressure due to pump 20 applied on the inlet flow passage 503. Thus, the inflow of fluid to the fluid chamber 501 from the side of the inlet flow passage reduces according to this pressure, and the outflow from the outlet flow passage 511 increases.

Consequently, a check valve installed on the inlet flow passage side, as in the fluid injection device according to the Japanese Unexamined Patent Application, First Publication No. 2005-152127, is not required.

However, inertance L1 of the inlet flow passage 503 is greater than the inertance L2 of the outlet flow passage 511; therefore, the increase in fluid discharged from the outlet flow passage is greater than the decrease in the inflow of the fluid to the fluid chamber 501 from the inlet flow passage 503. So the flow discharge in pulse form is generated to the connection flow passage 201, that is a pulsed flow is generated.

The pressure variation at the time of this discharge is transmitted to within the connection flow passage tube 200; that is, fluid is injected from the fluid injection opening 212 of the nozzle 211 at the front end.

Here, since the diameter of the fluid injection opening 212 of the nozzle 211 is smaller than the diameter of the outlet flow passage 511, the fluid is injected at a higher pressure as high speed droplets in pulse form.

On the other hand, the fluid chamber 501 is in a vacuum state immediately after rise in pressure because of the mutual interaction between the reduction in fluid inflow rate from the inlet flow passage 503 and the increase in fluid outflow from the outlet flow passage 511.

As the result, after a fixed period of time, the fluid in the inlet flow passage 503 returns to the flow toward the fluid chamber 501 at the same speed as before the action of the piezoelectric element 401 because of both pressure of the pump 20 and the vacuum state within the fluid chamber 501.

If the piezoelectric element 401 extends after the flow of fluid in the inlet flow passage 503 is restored, the pulse flow from the nozzle 211 can be continued and fluid can be injected.

Next, the action of removal of air bubbles in the fluid chamber 501 is described here.

During the operation of the pulse generation section 100 described above, swirl flow occurs in the fluid chamber 501, and the air bubbles included in the fluid are discharged outside the outlet flow passage 511 immediately. Because the fluid chamber 501 has a substantial rotating body shape and includes the inlet flow passage 503 as a swirl flow generation section, and also because the outlet flow passage 511 is formed in an open condition near the rotating axis of the substantial rotating body shape.

Accordingly, even during a very small volume change in the fluid chamber 501 due to the piezoelectric element 401, pressure variation is not hindered by air bubbles, and adequate rise in pressure can be obtained.

Consequently, according to the first embodiment 1, the initial operation can be started without priming operation because fluid is supplied to the inlet flow passage 503 at constant pressure from the pump 20 and because fluid is supplied to the inlet flow passage 503 and the fluid chamber 501 even when the drive of the pulse generation section 100 is in the stopped state.

Moreover, the liquid pressure increases above that in the outlet flow passage 511 since fluid is discharged from the fluid injection opening 212, which is smaller than the diameter of the outlet flow passage 511; therefore, high speed fluid injection can be attained.

Furthermore, the connection flow passage tube 200 possesses adequate rigidity to transmit the pulses of the fluid flowing from the fluid chamber 501 to the fluid injection opening 212. Thus, the pressure propagation of fluid from the pulse generation section 100 is not hindered, and the desired pulse flow can be injected.

Since the inertance of the inlet flow passage 503 is set greater than the inertance of the outlet flow passage 511, an increase occurs in the outlet flow passage 511 in the outflow rate that is greater than the decrease in the inflow rate of the fluid to the fluid chamber 501 from the inlet flow passage 503, and fluid in pulse state can be discharged into the connection flow passage tube 200.

Therefore, advantageous effects can be obtained such as: a check valve need not be installed on the side of the inlet flow passage 503 as in the Japanese Unexamined Patent Application, First Publication No. 2005-152127, the construction of the pulse generation section 100 can be simplified, internal parts can be cleaned easily, and the concern about durability when using a check valve is eliminated.

By setting the inertance of both the inlet flow passage 503 and the outlet flow passage 511 adequately great, and by abruptly reducing the volume of the fluid chamber 501, the pressure in the fluid chamber 501 can be increased steeply.

The construction can also be simplified by using piezoelectric element 401 and diaphragm 400 as the volume varying section, which can result in further miniaturization of the device.

The maximum frequency of for volume change of the fluid chamber 501 can be made greater than or equal to 1 kHz, which is ideal for injection at high speed pulse flow.

By generating swirl flow in the fluid in the fluid chamber 501 by the swirl flow generation section, the fluid presses against the fluid chamber in the circumferential direction because of the centrifugal force of the fluid, and the air bubbles included in the fluid near the axis of the substantial rotating body shape become concentrated at the central part of the swirl flow, and these air bubbles can be removed from the outlet flow passage 511 formed at a portion which is closer to the axis of the substantial rotating body shape.

As a result, the reduction in pressure amplitude due to accumulation of air bubbles in the fluid chamber 501 can be prevented, and stable operation of the pulse generation section 100 can be continued.

Moreover, since the swirl flow generation section is formed by the inlet flow passage 503, swirl flow can be generated without using a special swirl flow generation section.

Also, a groove-shaped inlet flow passage 503 is formed on the peripheral edge of the sealing surface 505 of the fluid chamber 501, an inlet flow passage 503 can be formed as the swirl flow generation section without increasing the number of parts.

Moreover, since a reinforcing plate 410 is formed on the upper surface of the diaphragm 400, and since the diaphragm is driven taking the periphery of the opening of the reinforcing plate 410 as the support point, stress concentration does not occur easily, and the durability of the diaphragm 400 can be enhanced.

If the corners of the joining surface of the reinforcing plate 410 and the diaphragm 400 are rounded, the stress concentration of the diaphragm 400 can be further relaxed.

If the reinforcing plate 410 and the diaphragm 400 are stacked and fixed as an integral body, the assembly of the pulse generation section 100 can be improved, and the reinforcement of the peripheral edge of the diaphragm 400 can also be made more effective.

The influence of the inertance of the connection flow passage 504 on the inlet flow passage 503 can be suppressed by providing fluid basin 507 for collecting the fluid at the connection of the inlet flow passage 503 and the connection flow passage 504 on the inlet side supplying fluid from the pump 20.

Moreover, since a ring-shaped packing 450 is separately disposed at a position in the circumferential direction of the diaphragm 400 on the connection surface between the upper case 500 and the lower case 301, the leakage of fluid from the fluid chamber 501 is prevented, and the pressure drop in the fluid chamber 501 can also be prevented.

Second Embodiment

Next, the pulse generation section related to the second embodiment of the invention is described here referring to the drawings of the same.

The second embodiment has a swirl flow generation plate including the inner peripheral wall of a fluid chamber and inlet flow passage as the swirl flow generation section.

Other than the swirl flow generation section, the construction is similar to that of the first embodiment described above, so the explanations are omitted here. The same reference numerals as in the first embodiment are attached to the functional members that are the same in the first embodiment.

FIG. 4 is a plan view of the swirl flow generation plate 550, and FIG. 5 is a cross-sectional view of the pulse generation section 100 in which the swirl flow generation plate 550 is assembled.

In FIG. 4, the swirl flow generation plate 550 has an opening formed at its central part; however, the peripheral part of this opening has the inner peripheral wall 551a of the fluid chamber 551 formed therein.

Also, the inlet flow passage 558 is formed as the swirl flow generation section in the fluid chamber 551, and a fluid basin 557 is formed in the part connecting the connection flow passage 504 on the inlet side.

The shape of the inlet flow passage 558, fluid basin 557 and inner peripheral wall 551a conform to the shape of the inlet flow passage 503, the fluid basin 507, and the inner peripheral wall 501a (see FIG. 3) described in the first embodiment above.

The swirl flow generation plate 550 may be formed by processing methods such as pressing process, etching process, or electric discharging process.

As shown in FIG. 5, the swirl flow generation plate 550 is stacked and disposed on the upper surface of the diaphragm 400, and is pressed and brought into contact with the peripheral face of the sealing surface 505 of the upper case 500 and the lower case 301.

Consequently, according to second embodiment mentioned above, by forming the swirl flow generation section by the swirl flow generation plate 550, the inlet flow passage 558, the inner peripheral wall 551a and the fluid basin 557 can be formed by the same manufacturing process; thus, the mutual positional accuracy can be enhanced.

Also, the swirl flow generation plate 550 is a single body, and can be formed by the pressing process, etching process or electric discharge process. The manufacturing method may be arbitrarily selected to suit the desired size such as flow passage length, width, thickness, and other shape conditions.

Moreover, if a swirl flow generation plate having cross-sectional area of inlet flow passage and flow passage length of a plurality of types of passages are available and by selecting swirl flow generation plate, the desired inertance of the inlet flow passage can be easily selected.

Third Embodiment

Next, the third embodiment of the invention is described here referring to the drawings.

The third embodiment has a swirl flow generation plate and diaphragm stacked and attached in intimate contact as an integral body.

Other than the swirl flow generation section, the construction is similar to that of the second embodiment described above, so the explanations are omitted here. The same reference numerals as in the second embodiment are attached to the functional members that are the same in the second embodiment also.

FIG. 6 is a plan view of the swirl flow generation plate 550 and the connected diaphragm 400 related to the third embodiment. FIG. 7 is a cross-section view taken along the line A-A shown in FIG. 6.

The swirl flow generation plate 550 is attached in intimate contact as an integral body with the diaphragm 400 in FIGS. 6 and 7.

The swirl flow generation plate 550 and the diaphragm 400 may be attached to each other by attaching structure such as bonding using adhesive, by solid state diffusion bonding, welding or the like. It is preferable that the swirl flow generation plate 550 and the diaphragm 400 be in close contact at the connecting face.

According to this third embodiment, the swirl flow generation plate 550 is made from a thin plate. An opening that forms the inner peripheral wall 551a of the fluid chamber 551 and the inlet flow passage 558 is provided.

Slender peninsular-shaped members are formed in the connection 559 at which the opening and the inlet flow passage 558 are connected.

Since the high pressure state and the vacuum state occur repetitively in the fluid chamber 551, the structural strength of the slender peninsular-shaped members mentioned above may be inadequate.

However, adequate structural strength can be obtained by integrating the diaphragm 400 and the swirl flow generation plate 550.

Another advantage is that handling is easy during assembly.

Fourth Embodiment

Next, the fourth embodiment of the invention is described here referring to the drawings.

In the fourth embodiment, an additional reinforcing plate is formed to further strengthen the structure of the second embodiment mentioned above.

Other than the additional reinforcing plate in the swirl flow generation section, the construction is similar to that of the second embodiment described above, so the explanations are omitted here. The same reference numerals as in the second embodiment are attached to the functional members that are the same in the second embodiment also.

FIG. 8A is a plan view of the connected state between the swirl flow generation plate 550 and the reinforcing plate 410 related to the fourth embodiment.

FIG. 8B is a cross-sectional view taken along the line B-B shown in FIG. 8A.

In FIGS. 8A and 8B, the swirl flow generation plate 550 has a similar shape as that in the second and third embodiments. The reinforcing plate 410 has a similar shape as that in the first embodiment. Both members are stacked, and are attached in intimate contact with each other as an integral body by fixing structure such as an adhesive, solid state diffusion bonding, welding or the like at the connecting face.

The swirl flow generation plate 550 and the reinforcing plate 410 is assembled in the pulse generation section 100 in the attached and intimate contact state.

FIG. 9 is a cross-sectional view of the assembled state of the joined swirl flow generation plate 550 and the reinforcing plate 410 in the pulse generation section 100.

In FIG. 9, the swirl flow generation plate 550 and the reinforcing plate 410 are disposed in the integrated state on the upper surface of the diaphragm 400.

Also, the swirl flow generation plate 550 and the reinforcing plate 410 are pressed and brought into contact with the peripheral face of the sealing surface 505 of the upper case 500 and the lower case 301.

After preparing plate members that constitute the swirl flow generation plate 550 and the reinforcing plate 410, the plate member constituting the swirl flow generation plate 550 is joined to the plate member constituting the reinforcing plate 410, and the inlet flow passage 558, fluid basin 557 and inner peripheral wall 551 of the swirl flow generation plate 550 may be formed by half-etching, and the inner peripheral wall 410a of the reinforcing plate 410 may be formed by etching.

Even if the diaphragm 400 and reinforcing plate 410 are joined, and the swirl flow generation plate 550 is assembled and constructed as a single structure, the diaphragm 400, the reinforcing plate 410 and the swirl flow generation plate 550 may be stacked, and attached in intimate contact with each other.

Consequently, according to the fourth embodiment mentioned above, by stacking and attaching the swirl flow generation plate 550 and the reinforcing plate 410 in intimate contact with each other to form an integral body, the swirl flow generation plate 550 can be reinforced, and handling during assembly also becomes easy.

Also, by stacking and attaching the diaphragm 400 and the reinforcing plate 410 as an integral body, or by stacking and attaching the diaphragm 400, the reinforcing plate 410 and the swirl flow generation plate 550 in intimate contact with each other, the effects of the invention mentioned above work well.

Fifth Embodiment

Next, the pulse generating device related to the fifth embodiment of the invention is described here referring to the drawings of the same.

According to the fifth embodiment, the inlet flow passage is formed by tubular member that penetrates the fluid chamber and an exterior of the pulse generation section. The construction of the inlet flow passage is mainly described here.

With respect to other functional members, the same reference numerals as in the first embodiment are affixed and described here.

FIG. 10 is a cross-sectional view of the pulse generation section 100 related to the fifth embodiment taken along the line C-C shown in FIG. 11, while FIG. 11 is a plan view of the upper case 500 as viewed from the side of the lower case 301.

In FIGS. 10 and 11, the inlet flow passage tube 520 is to attach by insertion into the upper case 500 toward the fluid chamber 501.

The inlet flow passage tube 520 is made from a metallic tubular member, penetrates the outside of the upper case 500, and passes through up to the fluid chamber 501.

Accordingly, the inlet flow passage 521 formed in the inlet flow passage tube 520 connects with the fluid chamber 501.

When the inlet flow passage 521 is configured with the same conditions for the pulse generation section 100 and the inertance L1 of the inlet side shown in the first embodiment above, the cross-sectional area and the flow passage length are set the same as for the inlet flow passage 503 as shown in FIG. 3.

Here, the construction of attachment by insertion of the inlet flow passage tube 520 is described.

An insertion hole guide portion for inlet flow passage tube 514 is formed in the upper case 500 into which the inlet flow passage tube 520 is attached by insertion.

Inlet flow passage tube insertion holes 512 and 513 are formed in a substantially perpendicular direction from the surface of this insertion hole guide portion for inlet flow passage tube 514 toward the fluid chamber 501.

Low-melting point silver solder plating is provided on the inlet flow passage tube 520. After insertion in the inlet flow passage tube insertion hole 513, it is heated and fused by the silver solder. The inlet flow passage tube 520 and the upper case 500 are attached in intimate contact with each other, and the leakage of fluid from the fluid chamber 501 is prevented.

The front end of the inlet flow passage tube 520 is cut such that it does not protrude into the fluid chamber 501.

The method of attaching the inlet flow passage tube 520 may be selected from using adhesive, by press-fitting or the like. A method that can resist the pressure in the fluid chamber 501 and that does not generate leakage of fluid is preferable.

The fluid chamber 501 includes a groove formed at the connection of the lower case 301 with the upper case 500. The fluid chamber 501 has a substantial rotating body shape.

The inlet flow passage 503 is installed in a substantially tangential direction with respect to the inner peripheral wall 501a of the fluid chamber 501 as shown in FIG. 11.

Accordingly, a swirl flow can be generated in the fluid chamber 501.

A connection tube 25 connecting the pump 20 (see FIG. 1) is connected to the end in the outward direction of the inlet flow passage tube 520.

The end 25a of the connection tube 25 extends up to the inside of the inlet flow passage tube insertion hole 512. To minimize the clearance in the radial direction of the end 25a and the inlet flow passage tube insertion hole 512, the inlet flow passage tube 520 can be reinforced.

Although not illustrated, if the part of the inlet flow passage tube 520 protruding outside the upper case 500 is bent, the direction of connection of the connection tube 25 can be set arbitrarily, and the operability of the pulse generation section 100 can be improved.

Consequently, according to the fifth embodiment described above, if the inlet flow passage 521 is formed by the inlet flow passage tube 520, the cross-sectional shape of the inlet flow passage 521 can be made circular, and the resistance elements in the flow passage can be reduced.

Also, the cross-sectional area and the length of the tubular member can be easily set. Also, if various types of tubular members are kept ready beforehand, the cross-sectional area and the flow passage length of the inlet flow passage 521 can be easily set to match the settings of inertance on the side of the inlet flow passage 521.

This invention is not limited to the embodiments mentioned above; changes, modifications within the scope of realization of the objects of the invention are included.

Consequently, according to the first to the fifth embodiments described above, in the fluid injection device, a priming device (priming operation) is not necessary, performance degradation due to air accumulating in the fluid chamber during the operation is eliminated, and a simple construction with no check valve and with high reliability can be offered.

What is claimed is:

1. A surgical device comprising:
a pulse generation section that includes a fluid chamber whose volume is changeable, and an inlet flow passage and an outlet flow passage that are connected to the fluid chamber, the inlet flow passage including a curved portion;
a first connection flow passage connected to the outlet flow passage, having an end portion;
a second connection flow passage connected to the inlet flow passage;
a fluid injection opening formed at the end portion of the first connection flow passage, having a diameter smaller than a diameter of the outlet flow passage;
a connection flow passage tube including the first connection flow passage and having rigidity adequate to transmit pulses of fluid flowing from the fluid chamber to the fluid injection opening; and
a pressure generation section that supplies fluid to the inlet flow passage, wherein
inertance L is expressed by $L = \rho \times h/S$, where density of fluid is $\rho$, cross-sectional area of flow passage is S, and length of the flow passage is h, and
inertance L1 on the inlet flow passage is greater than inertance L2 on the outlet flow passage.

2. The surgical device according to claim 1, wherein
the pulse generation section includes a volume varying section for varying the volume of the fluid chamber, and the volume varying section includes a piezoelectric element that expands or compresses the fluid chamber, and a diaphragm.

3. The surgical device according to claim 1, further comprising:
a reinforcing plate that has an opening whose diameter is substantially equal to the diameter of the fluid chamber, and that is formed between a sealing surface on which the inlet flow passage is formed and the diaphragm.

4. The surgical device according to claim 3, wherein
the diaphragm and the reinforcing plate are stacked and attached in intimate contact with each other as an integral body.

5. The surgical device according to claim 1, further comprising:
a fluid basin that is formed at the connection between the second connection flow passage on the inlet side supplying fluid to the inlet flow passage from the pressure generation section and the inlet flow passage, and that collects fluid.

6. The surgical device according to claim 1, wherein
the inlet flow passage is formed by a tubular member that passes through the fluid chamber and an exterior of the pulse generation section.

7. The surgical device according to claim 1, further comprising:
a ring-shaped packing separately disposed at a position in the circumferential direction of the diaphragm.

\* \* \* \* \*